United States Patent [19]

Goldberg et al.

[11] Patent Number: 4,894,012

[45] Date of Patent: * Jan. 16, 1990

[54] PASSIVE DENTAL APPLIANCES OF FIBER-REINFORCED COMPOSITES

[75] Inventors: A. Jon Goldberg, West Hartford; Charles J. Burstone, Farmington, both of Conn.

[73] Assignee: The University of Connecticut, Farmington, Conn.

[*] Notice: The portion of the term of this patent subsequent to Jan. 5, 2005 has been disclaimed.

[21] Appl. No.: 121,178

[22] Filed: Nov. 16, 1987

[51] Int. Cl.$^4$ .............................................. A61C 7/00
[52] U.S. Cl. ............................ 433/215; 260/998.11; 433/6; 433/167; 433/212.1; 433/222.1; 523/115
[58] Field of Search ....................... 523/115, 116, 117; 433/199, 201, 202, 212.1, 222.1, 6, 167, 196, 215; 260/998.11

[56] References Cited

U.S. PATENT DOCUMENTS

| | | | |
|---|---|---|---|
| 3,675,327 | 7/1972 | Huget et al. | 433/215 |
| 4,107,845 | 8/1978 | Lee, Jr. et al | 523/116 |
| 4,312,917 | 1/1982 | Hawley | 428/375 |
| 4,321,042 | 3/1982 | Scheriher | 106/35 |
| 4,381,918 | 5/1983 | Ehrnford | 523/116 |
| 4,439,387 | 3/1984 | Hawley | 264/100 |
| 4,490,116 | 12/1984 | Deutsch et al. | 433/215 |
| 4,604,097 | 8/1986 | Graves, Jr. et al. | 433/201.1 |
| 4,681,544 | 7/1987 | Anthony | 433/215 |
| 4,718,910 | 1/1988 | Draenert | 433/202.1 |

FOREIGN PATENT DOCUMENTS 2028855 3/1980 United Kingdom ................ 523/116

OTHER PUBLICATIONS

"Intermediate Fiberglass Splints", J. Friskopp, Journal of Prosthetic Dentistry, 3/84, vol. 51, no. 3, pp. 334–337.
"Technique and Rational for Splinting", Neaverth et al., Clinical Reports, JADA, vol. 100, 1/80, pp. 56–63.
"The multistrand Retainer and Splint", Becker et al., Am. J. Orthod., 6/84, vol. 85, no. 6, pp. 470–474.
"Implant-Fixed Dental Bridges from Carbon/Graphite Fibre Reinforced Poly (Methyl Methacrylate)", Bjork et al., Bio-Materials, 1986, vol. 7, Jan., pp. 73–75.
"Polymethylmethacrylate Reinforced with Carbon Fibres", C.K. Schreiber, L.D.S., Brit. Dental Journal, 1/5/71, pp. 29–30.
"The Clinical Application of Carbon Fibre/Polymer Denture Bases", Schreiber, L.D.S., Brit Dental Journal 7/2/74, pp. 21–22.
"Denture Base Acrylic Reinforced with High Modulus Fibre", A.M.H. Grave et al., Dent. Mater., 1985, vol. 1, pp. 185–187.
"The use of a Clear Pliable Film to FOrm a Fiber--Glass-Reinforced Splint", M.F. Levenson, JADA, vol. 112, 1/86, pp. 79–80.
"Resin Fiberglass Bonded Retainer", M. Diamond, JCO, 3/87, vol. 21, no. 3, pp. 182–183.
"The Effect of Carbon Fiber Orientation on the Fatigue Resistance and Bending Properties of Two Denture Resins", J. DeBoer et al., Jour. Pros. Dent. 1/84, vol. 51, no. 1, pp. 119–121.
"Aramid Fiber Reinforcement of Acrylic Appliances", R. H. Mullarky, JCO, vol. XIX, no. 9, pp. 655–658, 9/85.
"Development of Carbon/Graphite Fiber Reinforced Poly (Methyl Methacrylate) Suitable for Implant-Fixed Dental Bridges", I.E. Ruyter et al., Dent. Mater., 1986, vol. 2, pp. 6–9.

*Primary Examiner*—Paul Liberman
*Assistant Examiner*—Linda D. Skaling
*Attorney, Agent, or Firm*—Chilton, Alix & Van Kirk

[57] ABSTRACT

Disclosed is a dental appliance system having use as an orthodontic retainer, bridge, space maintainer, splint and the like, the improvement wherein a structural component thereof is formed from an effective fiber-reinforced composite material comprising a polymeric matrix and a reinforcing fiber component embedded within the matrix, the reinforcing fiber component comprising at least 20% by weight of the composite material and being substantially fully wetted by the polymer matrix, the composite material being substantially free of voids and having a modulus of elasticity greater than $0.5 \times 10^6$ psi.

14 Claims, No Drawings

PASSIVE DENTAL APPLIANCES OF FIBER-REINFORCED COMPOSITES

BACKGROUND AND SUMMARY OF THE INVENTION

The present invention relates to dental appliances and structural components thereof. More particularly, it is concerned with passive or nonforce-imparting dental appliances and with dental systems using passive components made from fiber-reinforced composite plastic materials.

Dental appliances are employed for a wide range of purposes, but generally can be classified into force-imparting and nonforce-imparting applications. The former are generally associated with orthodontic appliances where forces are used to move teeth and bone to more desirable positions. Our prior developments of orthodontic systems using beta titanium metallic alloys and fiber-reinforced composites in orthodontic systems are reported, respectively, in U.S. Pat. No. 4,197,643 and in copending U.S. Patent Application Ser. No. 817,925, now U.S. Pat. No. 4,717,341.

Nonforce-imparting or passive dental appliances are intended to restore or replace teeth, to retain natural teeth in a desired position subsequent to orthodontic treatment or tooth loss, to prevent migration and to give added support to a weakened periodontium. These appliances often include structural components which function as bars, wires, beams, posts, clasps and other complex shapes, etc. For example, retainers typically employ a wire partially contoured to the teeth to maintain their positions. The wires may be imbedded in a plastic portion which, along with embedded wire clasps, retain the appliance in position. Periodontal splints employ a wire bonded to the teeth to stabilize them following periodontal surgery or for other reasons. Children often are fitted with a space maintainer, which is an appliance that incorporates beams attached to the teeth on either side of an edentulous site or connected to molars on either side of the mouth. Removable partial dentures employed heretofore, are metallic frameworks to which prosthetic teeth are fastened. Fixed prosthetic appliances, including traditional bridges and acid-etched bridges, incorporate bars and beams for structural integrity. Other passive dental appliances also incorporate structural parts.

The devices described above and other passive dental appliances could be divided into the following five categories of appliances: fixed, removable, fixed-removable, tooth replacement, and passive orthodontic and temporo-mandibular joint (TMJ), appliances. Fixed appliances or retainers are bonded directly to the teeth and are used to retain teeth after orthodontic treatment or to serve as periodontal splints. Removable appliances or retainers are not directly bonded to the teeth but instead are carried or supported by soft tissue and teeth. Removable appliances are used for retention and tooth replacement. Fixed-removable appliances or retainers also are carried or supported by soft tissue and teeth but, in addition, they are connected to fixed attachments that are separately bonded or attached to the teeth. Fixed tooth replacement appliances are used to replace missing teeth, temporarily or permanently, or to act as space maintainers. The materials and techniques described herein also can be used to restore individual missing teeth with a band, crown, veneer, or smaller restoration. Finally, passive orthodontic and temporo-mandibular joint appliances transmit or use muscle forces to alter growth, to guide dental development, and to alter TMJ and muscle functions or habits. Examples include functional appliances, headgears, bite opening and disc recapturing appliances and lip bumpers. Although these five categories of appliances are by themselves passive and nonforce-imparting, they can be used in combination with force imparting appliances as separate or integral units.

Traditionally, the types of appliances described have been constructed from either metal alloys or polymers. Alloys such as chromium-cobalt-nickel, Cr-Co-Ni, are commonly used in partial denture frameworks. Fixed prosthodontic devices employ gold-based, palladium-based and Cr-Co-Ni alloys. Retainers and periodontal splints incorporate stainless steel wires or bars while space maintainers us stainless steel wires. The polymer used in virtually all dental structural appliances, whether it be a component, as in a retainer, or the entire appliance, as with a complete denture, is an acrylic polymer such as polymethylmethacrylate (PMMA).

There are various characteristics which are important for any nonforce-imparting dental structural component. Probably the most important of these is high stiffness and strength with minimum bulk. The structural component is often maintaining or retaining the relative positions of dental tissues or acting as part of a prosthetic appliance. In each case, the component is expected not to deflect or deform under stress. Therefore high rigidity or stiffness is important. Appliance stiffness is dependent on the moment of inertia of the geometric shape of the device and the modulus of elasticity of the material. To a limited practical degree bulk and modulus can be interchanged to maintain stiffness. For example, a fixed prosthetic appliance made from a Cr-Co-Ni alloy can be slightly thinner than one made from a gold-based alloy because the Cr-Co-Ni alloy has a greater modulus of elasticity. In addition to stiffness and strength, other important characteristics for a nonforce-imparting dental component include ease of processing and appliance fabrication, accuracy of fit, esthetics, ease of joining to itself and to other materials, ease of bonding to hard dental tissue, biocompatibility and structural stability.

Currently no single dental material or appliance design completely satisfies all of these needs. In general, the metal alloys have superior mechanical properties, but require special laboratory processing, are difficult for the clinician to form and adjust and are not aesthetic. Some alloys contain potentially non-biocompatible elements such as nickel and beryllium. The structural polymeric dental materials such as PMMA are easier to process, although the procedures still are usually performed in a special dental laboratory. More significantly, the stiffness and strength of the polymeric materials are low, and require compensating bulk. Some appliances, like retainers, employ both metal and plastic to take advantage of the favorable features of each.

The dental literature contains reports of attempts at improving the mechanical properties of the acrylic polymers by reinforcement with fillers. However, successful applications have been with restorative filling materials that incorporate a particulate filler in a methacrylate matrix such as bisphenol-A glycidyl methacrylate (BIS-GMA) or polyurethane dimethacrylate. These particular filled plastics are not fiber-reinforced and are used as filling materials, cements or veneers, but not as structural components of the type described herein.

Reported attempts of using fiber reinforcement for structural components have been unsuccessful. Two recent reports have been by R. H. Mullarky, Journal of Clinical Orthodontics Vol 19, No. 9 p 655-8, Sept. 1985 and by DeBoer, et. al, Journal of Prosthetic Dentistry Vol 51, No 1 p. 119-121 Jan. 1984. In both cases, the authors attempted to place fibers into traditional dental acrylic, while simultaneously forming the desired appliance. While both articles report some improved properties with reinforcement, the degree of improvement is much less than would be expected from an effective fiber reinforced composite. In addition, the techniques are performed by hand thereby possibly causing contamination of the fiber surface and a likely deterioration in the wetting characteristics at the resin-fiber interface. Splints reported by M. F. Levenson, CDS Review pages 23-25, September, 1986, appear to have similar deficiencies. Finally, the techniques are difficult to carry out and are not reliable. DeBoer states that the technical difficulty associated with incorporating the fibers "may outweigh any potential advantage."

It is believed the reason for the earlier lack of success in achieving the expected mechanical properties is that effective composite materials were never formed. The approaches are appealing because the composite and the appliance were formed simultaneously and traditional dental materials and techniques were used. However, the data shows that the strength and stiffness or modulus of elasticity were below expectations. It is quite likely that limited fiber loading coupled with either poor wetting and/or the presence of voids at the resin-fiber interface could account for the poor results.

Grave, Chandler and Wolfaardt, Dent. Mater. Vol 1, p 185-187 (1985) attempted to reinforce dental acrylics with loosely woven carbon or Kevlar fiber mat. Their results with bending tests of standard test specimens showed a modest improvement in properties for one dental acrylic, and a decrease in strength and stiffness for a second.

The present invention obviates these technical difficulties and provides nonforce-imparting or passive dental components and appliances that possess a preferred combination of properties compared to polymeric compositions used herebefore. This includes not only greater stiffness and strength but also generally higher mechanical properties than those exhibited by the commonly used dental polymers. They are more esthetic and easier to process, form and adjust than dental metallic alloys, thereby allowing for superior and unique designs. Included in this object is the provision for a passive dental component or appliance made from a preformed effective fiber-reinforced composite material via an improved two step process.

Another object of the present invention is to provide passive dental components and appliances of the type described using a two step technique that optimizes the wetting of the fibers while obviating the presence of voids, thereby enabling the incorporation of significantly higher amounts of fiber with concomitant increases in strength and other desired mechanical properties. Included in this object is the provision for the initial production of an effective composite material and the subsequent formation of the dental component from that material.

Still another object of the present invention is to provide passive dental appliances of the type described having improved fiber distribution and dispersion in a fiber-reinforced composite material while avoiding the contamination and deterioration of the fiber-resin interface heretofore associated with hand placement of the fibers. Included in this object is the provision for the effective use of a wide range of resins in the dental components as well as a variety of processing techniques.

A further object of the present invention is the provision for fiber reinforced composite passive appliances such as fixed retainers that can be bonded directly to the teeth and other components; are easily and directly formed into complex shapes requiring minimum skill and simple procedures yet are more intricate, give greater control over tooth position, have lower appliance bulk with comfort, are esthetically pleasing and are not dependent on patient cooperation.

Using the present invention, removable appliances have greater strength with less bulk, allowing superior resistance to fracture and deformation. Their smaller size facilitates patient acceptance and cooperation, less palatal coverage that allows more normal taste during mastication and less complex retention mechanisms. Additionally, the fixed tooth replacement appliances are stronger than existing polymer bridges, require simple direct and laboratory procedures, are relatively non-invasive to adjacent teeth and are esthetically pleasing.

Passive appliances employing the present invention, may have complex curvatures which are more functional and comfortable, are simple to fabricate and most importantly are stronger and more durable. For example, for headgear the invention allows for more complex configurations that are stronger and more efficient. These appliances also can have less bulk, possess better aesthetics and are more comfortable for the patient.

Other objects and advantages will be in part obvious and in part pointed out more in detail hereinafter.

These and related objects are achieved in accordance with the present invention by providing a passive dental appliance or structural component thereof fabricated from an effective fiber reinforced composite material comprised essentially of a polymeric matrix and a fiber component embedded within the matrix. The fiber component of the composite material constitutes greater than 20 percent by weight of the composite material and the modulus elasticity of the composite is greater than $0.5 \times 10^6$ psi. The beneficial results of the present invention are achieved by utilizing a system that employs a two-step procedure. First, an effective fiber-reinforced composite material is produced having the requisite stiffness and strength characteristics, fiber orientation and void free wetting of the fibers. The effective composite material is thereafter formed into the dental device; to achieve improved aesthetics coupled with ease of processing and structural stability. This two-step process allows for the optimum development of the most advantageous mechanical properties.

A better understanding of the invention will be obtained from the following detailed description of the illustrative applications of the invention including the several components of the invention and the relation of one or more of such components with respect to each of the others, as well as the features, characteristics, compositions, properties and relation of elements described and exemplified herein.

DESCRIPTION OF THE PREFERRED EMBODIMENT

As mentioned, the present invention provides for an improved dental appliance and structural components thereof by employing a two step process that involves initially forming or producing an effective fiber-reinforced composite material and thereafter forming the dental device therefrom. This procedure allows for the optimum development of the mechanical properties of the composite without necessarily being confined by concern relating to the formation of the dental appliance. Of course, it will be appreciated that the formation of the effective fiber reinforced composite, as a practical matter, may be achieved almost simultaneously with the formation of the dental appliance. However, for clarity of description and ease of understanding, the technique of the present invention has been separated into two separate and distinct steps whereby, first, the effective fiber reinforced composite material is produced and, secondly, the dental appliance is formed from that composite.

There are several aspects to the successful production of an effective fiber reinforced composite material. These include:

(1) the effective wetting of the fibers by the matrix and the associated coupling between the fiber and matrix components;

(2) the provision for an even and uniform distribution of the fibers throughout the matrix material;

(3) the proper fiber orientation within the matrix for the specific characteristics and properties desired within the ultimate dental appliance or component, (4) the elimination of voids or air pockets within the composite material, and (5) the proper selection of the appropriate fiber and matrix materials.

As mentioned in our copending Application Ser. No.817,925,now U.S. Pat. No. 4,717,341 the content of which is incorporated herein by reference, the stiffness of an appliance is proportional to that material's modulus of elasticity. For currently used plastic materials in the dental field the modulus is well below $1.0 \times 10^6$ and generally is in the region of $0.3$–$0.5 \times 10^6$ psi. Materials 1 that would provide a modulus above that range and preferably about $1.0 \times 10^6$ psi or more would significantly enhance the versatility of dental procedures and enable a more uniform progression in the stiffness or flexibility characteristics needed for dental devices. Advantageously, the effective fiber-reinforced composites of the present invention fall within the desired range or modulus region and can be designed and engineered to provide a continuous selection of stiffness and strength over a wide range by adjusting the characteristics of the effective composite material instead of the conventional approach of adjusting shape and cross section only.

The composite material utilized in accordance with the present invention is composed of two major components, a polymeric matrix and fibers embedded within the matrix. The fibers preferably take the form of long continuous filaments, although these filaments may be as short as 3 to 4 millimeters. Alternatively, shorter fibers of uniform or random length might also be employed. Where the composites take the form of elongated wires, the fibers are at least partially aligned and oriented along the longitudinal dimension of the wire. However, depending on the end use, the fibers may be otherwise oriented, even to the point of being normal or perpendicular to that dimension to provide specific characteristics such as maximum torsional strength. The composite material may be used to produce devices having unusual properties that can be tailored through the use of various fabricating techniques including the orientation of the fibers within the composite material as well as the percentage of fibers utilized. This feature is particularly important where the particular dental appliance requires certain three dimensional characteristics and control of the system in all dimensions is critical.

Although a variety of fibers may be employed, the most commonly used fibers are glass, carbon and/or graphite, and polyaramid fibers such as the fibers sold under the trade name "Kevlar". Other materials such as polyesters, polyamides and other natural and synthetic materials compatible with the particular matrix also may be employed to provide selected properties.

The continuous filaments or fibers used in accordance with the present invention will vary in fiber diameter or denier as well as in fiber length, and it is preferred to utilize a range of fiber diameters. Where synthetic materials are employed, the diameters may vary from about 1.5 to 15 denier while for inorganic materials such as glass the fibers are usually very fine, with diameters falling in the low micrometer to submicrometer range. A typical range for glass fibers is about 0.3 to 25 micrometers with the preferred range being about 3 to 12 micrometers. Carbon and graphite fibers are typically near the low end of the range for glass and preferably exhibit diameters of about 3 to 12 micrometers. Those fibers may have an irregular cross section or may be circular or "dog-bone" in configuration.

In accordance with the present invention, it is preferred that a predominant number of fibers be aligned along the longitudinal dimension of the wire. The orientation results in some degree from the production techniques used to form the resultant product, but also is specifically designed into these devices. These techniques include molding, such as compression molding, but the preferred technique is a form of extrusion known as pultrusion. In the pultrusion process, a sizing or coupling agent is applied to the continuous filaments to improve the wetting thereof by the polymeric matrix and enhance matrix fiber bond. The treated fibers are aligned and maintained in position as they are pulled through a bath of matrix polymer. The fibers are maintained under tension while the matrix material, which is in a near liquid state, intimately engages and effectively wets the fibers and results in more effective coupling and hence improved mechanical properties. Physically holding the fibers in position helps to assure even and uniform distribution of the fibers in the final composite. As the fibers and matrix leave the polymer bath, the composite may pass through a series of rollers or dies to develop a uniform exterior or outside dimension and assure that the fibers do not protrude through the outside matrix surface.

The continuous fibers are usually disposed in a parallel array relative to each other and are aligned along one dimension such as the major dimension of the device being produced. The continuous filament composite material is capable of providing a wire having a modulus of elasticity beyond the range available with polymeric materials used heretofore. For example, a continuous filament material can be formulated to provide a composite that exhibits a modulus in the range of 1.01 to $60 \times 10^6$ psi and greater. With glass or synthetic materials the modulus may be up to about $35 \times 10^6$ psi while with carbon fibers the modulus may fall within a range up to $40$–$50 \times 10^6$ psi.

The polymeric materials employed as the matrix for the reinforcing fibers preferably are fully polymerized thermoplastic materials although a wide variety of polymeric materials, may be employed, including partially polymerized thermosetting materials. The thermoplastics allow ease of formability and the stiffness, strength, springback and creep resistance preferable for passive applications. For example, the polymeric material may include polyamides such as nylon, polyesters, glycol esters such as polyethylene terephthalate glycol, polyolefins such as polypropylene or polyethylene, polyimides, polyarylates, polyurethanes, styrene, styrene acrylonitrils, ABS, polysulfones, polyacetals, polycarbonates, polyphenylene sulfides, or a wide variety of other polymeric compositions including vinylesters and epoxy type materials. Among this group, the thermoplastic materials are preferred since they are not as brittle, exhibit greater toughness and more readily facilitate the second phase of the dental appliance forming operation.

As indicated, the final properties of the fiber reinforced composites may vary not only with the individual materials utilized in the compositions, but also with the volume ratio of fiber to polymer matrix a well as the diameter or denier of the particular filaments being employed. The percent fiber content and wetting are related in that it is easier to wet a lower percentage of fibers. However, as the fiber content increases it becomes more difficult for the resin to penetrate through the fiber bundles and thoroughly impregnate all of the individual fibers. The fiber content reported for devices in the dental prior art is relatively low, being reported at less than about 20 percent. This is probably due to an inability to wet larger percentages of fibers using standard dental procedures. Larger fiber contents in prior material would probably lead to reduced mechanical properties, due to ineffective wetting and voids.

The volume percent of fibers in each composition may vary within a wide range extending from as little as about 5 percent up to about 85 to 90 percent of the total composition of the effective composite material. Generally at least 15-20 percent fiber loading is utilized while the preferred materials contain from 40 to 60 percent continuous filaments. As can be expected, the stiffness or flexure modulus of the material will increase with increasing amounts of fiber as will the yield strength of the material.

In accordance with the present invention, the reinforcing fibers are not placed by hand. Rather, mechanical means are used to insure optimum distribution and dispersion of the fibers. The placement of the fibers by hand may cause contamination of the fiber surface, resulting in deterioration of the resin-fiber interface. The mechanical means employed can incorporate a variety of processing techniques including, but not limited to open molding; matched-die processes; resin injection molding; sheet, dough and bulk molding; compression molding; transfer molding; reaction injection molding; injection molding; press molding; autoclave molding; and extrusion such as pultrusion. All of these methods specifically must include sufficient flow of the resin around the fibers to enhance wetting. This becomes more important as the fiber content is increased to insure penetration of the resin through the fiber bundles and complete wetting of all fibers. In the pultrusion process used to form the high fiber content reinforced thermoplastics, the fiber strands are pulled through the resin and follow a convoluted channel which forces the resin against the fibers as they are drawn against the sides of the channel. This technique is the subject of U.S. Pat. Nos. 4,439,387 and 4,312,917. Those patents depict and describe the squeegee action of the extrusion die that causes assured intimate contact between the fibers and resin coupled with relative movement therebetween. All of these factors, including the tension on the fibers, contribute to the improved wetting of the fibers.

With the thermosetting resins, the fiber is incorporated into the resin and thoroughly wetted with the help of pressure and/or mechanical means. The resin is partially polymerized to the stage where the composite can maintain its integrity, yet can still be easily formed by hand at room temperature. The composite is then formed to the desired shape. This is followed by final polymerization or curing by various means including chemical, heat, light or other forms of radiation. The pre-formed composite or "pre-preg" does not possess its final mechanical properties, but complete fiber distribution and resin impregnation has occurred.

Flexural properties of typical composites of polyethylene terephthalate glycol, PETG, with 55% continuous glass were determined on samples having typical dimensions for dental appliance, nominally $0.025 \times 0.025 \times 1$ inch long. Specimens were exposed to dry and wet conditions at 37°, 45° and 50° C. for times of up to two months. Generally, the flexural modulus varied between 1.5 and $2.5 \times 10^6$ psi and there was no apparent degradation after one month even at temperatures as high as 50° C. Similar results were obtained for the maximum moment and the maximum bending angle. Comparable results for all three parameters were found under wet conditions. Additional testing was conducted using PETG and other thermoplastic resins with 40, 50 and 60% continuous glass fiber. The flexure modulus of 10 mm long samples of PETG was found to vary from 1.5 to $2.3 \times 10^6$ psi. The mean moment at 1° permanent deformation was 1100 to 1300 gm-mm for the PETG. The ultimate moment for these same materials increased from 1330 to 1580 gm-mm as the glass content was increased from 40 to 60%.

The potential stability of passive appliances in the oral environment was evaluated with laboratory tests of stress relaxation, creep and hydrolytic stability. There was no deterioration in the flexural properties of straight lengths maintained in 45° deionized water for up to 3 months. Stress relaxation and creep were determined by maintaining one inch specimens at deflections of 10° to 50° in 37° C. water for 2 months. At various intervals the samples were removed. Both the permanent set and the moment necessary to maintain the original deflection was then measured. The moment decreased approximately 25% for all FRC, with most of the relaxation occurring in the first 3 days. Stress relaxation was considered clinically acceptable since the passive devices should impart no stress and therefore, there can be no decay. Passive appliances may be subjected to forces from chewing or other force-imparting components; nevertheless, deflection is relatively low.

The forming of the dental appliance can be accomplished directly on a dental cast from preformed bars, strips, or wires using a heat gun. In other applications a preformed shape is initially fabricated using a mold that is heated at optimum temperature under pressure in an oven or by a heat gun applying dry heat. The preformed shape allows arch forms and other complex shapes that more closely approximate the final dental appliance and hence, allows for greater ease of fabrication. Although the final dental appliance can be made precisely using a male-female mold, usually the preformed shape used for the final dental appliance is formed with a heat gun on the dental cast.

The final forming process for a dental appliance is accomplished using a dental cast which accurately duplicates both the hard and soft tissues in the mouth. The fiber-reinforced composite strip or bar is sealed or clipped to the cast and sections are sequentially heated until soft. A range of temperatures is used to optimize the forming temperatures. This can be achieved by using a rheostat-controlled electrical heat gun that delivers a stream of hot dry air through a variable diameter nozzle. During fabrication, the temperature also can be controlled in part by the distance of the heat gun nozzle from the component. The temperatures used depend on the matrix-fiber composition. The PETG-glass composites that have been fabricated into dental appliances typically use temperatures in the 80°–120° C. range.

Following the softening of the preformed component, it is molded to the intricate detail of the teeth or soft tissues by hand using instruments to press the FRC against the dental model. An alternate method is to form the appliance using a silicone mold or rubber strip to produce more uniform pressure. After initial forming, a stress relieving treatment may be performed to further enhance dimensional stability. The final dental appliance is cooled to room temperature before its removal from the cast.

The method used in clinical application has been primarily the use of dry heat by oven and the heat gun. Thus, it can be seen that various methods or techniques that control the application of heat to the parts can be used. Experiments have shown that an alcohol flame or a dry heat source can form parts without a mold using the techniques employed by glass blowers.

The forming of the thermoset dental appliance is accomplished by contouring the composite to a dental cast with hand pressure and suitable instruments. In some instances, the contouring can be carried out directly in the mouth. Following the forming of the passive dental appliance to the intricate detail required, the full polymerization is produced either chemically or by a radiant energy cure technique.

Bonding experiments with the glass fiber, thermoplastic matrix composites were conducted using heat, heat-ultrasonic heating techniques and commercial orthodontic adhesives. With the proper technique, shear strengths of approximately 2000 psi were obtained with the commercial adhesives. Values of 1630 psi were obtained with PETG-50% glass. Shear bond strengths of orthodontic brackets to enamel are typically 2000–3000 psi. Higher strengths were obtained with ultrasonic techniques. These joining techniques demonstrate the ability to bond passive appliances to the teeth and to fabricate complex shapes and join them by heating.

The cross-sections of various fiber reinforced materials made in accordance with the present invention has been evaluated microscopically. The fiber distribution is approximately uniform, but most importantly all fibers are thoroughly wetted by the thermoplastic resin and there are no apparent voids at the fiber-resin interface. This microscopic evaluation collaborates the mechanical property data and support the conclusion that there is effective reinforcement of the resin. The passive dental appliances have been placed in over twenty patients with the longest period for any one patient being about seven months. The appliances include an esthetic upper removable retainer, upper and lower bonded lingual retainers and bridges. The bridges have been used for replacing missing cuspids, lateral incisors and molars. All bridges have used acrylic teeth for the replacements. In one patient with a bonded lingual periosplint, the natural tooth to be extracted was sectioned and bonded directly to the appliance as a pontic.

The following examples are given in order that the effectiveness of the present invention may be more fully understood. These examples are set forth for the purpose of illustration only, and are not intended in any way to limit the practice of the invention. Unless otherwise specified, all parts are given by weight.

EXAMPLE I

An effective thermoplastic fiber-reinforced composite material was prepared using polyethylene terephthalate glycol as the matrix material and continuous glass filaments having a diameter of 13 micrometers as the fiber component. The reinforcing glass fibers or filaments were added to the extent indicated in Table I.

Using the resultant composite materials, retainers were formed on a plaster cast of a dental arch. Fixed lingual cuspid to cuspid and bicuspid to bicuspid, bonded lingual retainers were fabricated from 0.025" and 0.040" thick composite material. Widths varied from 0.040" to 0.120". The appliances were constructed from flat, pre-formed strips or strips in which the preform was further modified to form a 30 degree inner angle for better contouring with the teeth. The preformed composite strip was formed into an arch. The arch was further adapted by dry heat to the lingual surface of the teeth. A heat gun with a variable rheostat accurately controlled the forming temperature.

While holding one end of the strip against the lingual surface of the appropriate teeth, a warm stream of air was directed onto the adjacent section of the wire until it softened enough to be easily formed against the adjacent tooth. This process was continued until cuspid to cuspid, bicuspid to bicuspid and molar to molar retainers were fabricated. Upon cooling to room temperature, the composite demonstrated both a modulus of elasticity in excess of $2 \times 10^6$ psi and high strength. After forming, translucency was present, thereby insuring excellent esthetics. Formed PETG lingual retainers also were bonded to extracted teeth with conventional dental orthodontic adhesives. The joining was considered excellent. This clearly demonstrates the ease of fabrication, good esthetics and direct bonding capability.

As can be appreciated, the procedure for forming the lingual and labial retainers was extremely simple, required less skill and was more exacting than currently used methods which require forming of a metallic wire. The lingual retainer had the additional advantage of being able to be bonded directly to the teeth while providing excellent aesthetics and better adaptation to the teeth.

Additional fiber reinforced composite materials were prepared using the same pultrusion technique. The apparent modulus for 5 mm lengths is set forth in Table I.

TABLE I

| Resin | Fiber | % Fiber | Modulus ($\times 10^6$ psi) Mean | Range |
|---|---|---|---|---|
| PETG | E-glass | 60 | 2.07 | 2.03–2.15 |
| PETG | E-glass | 50 | 1.33 | 1.18–1.45 |
| PETG | E-glass | 40 | 1.23 | 0.77–1.50 |
| Urethane-1 | E-glass | 60 | 1.43 | 1.18–1.67 |
| Urethane-1 | E-glass | 50 | 1.06 | 0.63–1.53 |
| Urethane-1 | S-glass | 60 | 1.05 | 0.92–1.18 |
| Urethane-3 | S-glass | 60 | 1.44 | 1.29–1.60 |
| Urethane-3 | S-glass | 40 | 1.16 | 1.09–1.22 |
| Polycarbonate | E-glass | 60 | 0.96 | 0.88–1.00 |
| Nylon-12 | S-glass | 60 | 0.93 | 0.80–1.14 |
| Nylon-12 | E-glass | 60 | 0.92 | 0.76–1.10 |

EXAMPLE II

Using the same procedure as in Example I, 0.040" PETG-55% glass with 0.060" widths were used to fabricate molar to molar fixed appliances that were bonded directly to all of the teeth in the arch or selectively bonded to the right and left molars. A similar appliance was constructed on the labial surface of the tooth which was both intermittently and continuously bonded.

EXAMPLE III

A wrap-around, removable retainer was constructed for the upper arch. Labial PETG-60% glass wires 0.040"×0.080", and 0.040"×0.060" and 0.040"×0.050" were constructed. The labial wire continued posteriorly to the most posterior molar and then was joined on the lingual to an acrylic palate. This removable retainer offered high strength, and stiffness. Its many advantages include simple detailed contouring of the wire on the labial and buccal surfaces which is difficult, if not impossible, to do with a metal wire; added tooth control because of the occlusal gingival width of the strip and excellent esthetics.

EXAMPLE IV

Space maintainers were fabricated to hold a missing primary molar or permanent bicuspid space. PETG-glass strips using 60% fiber were formed and then connected to the teeth adjacent to the missing tooth on both the buccal and the lingual. These strips were then bonded to the teeth to preserve and hold the space.

EXAMPLE V

Periosplints were constructed of PETG-55% glass composite using strips 0.040"×0.060" or 0.040"×0.080" strips. These splints were constructed on both buccal and lingual surfaces for direct bonding. The technique used was similar to those described in Example I. The splints were continuously bonded and ran from molar to molar, bicuspid to bicuspid or cuspid to cuspid.

EXAMPLE VI

A three-tooth permanent or temporary bridge was constructed to replace a single lateral incisor. A 0.040"×0.160" PETG-glass strip was contoured between the central incisor and the cuspid to form a lingual bar. An acrylic tooth was ground to fit into the edentulous space. The contoured lingual bar was then joined to the acrylic tooth with dental adhesive and acrylic. A groove was placed in the acrylic tooth to hold the lingual bar to add further retention to the bridge. This bridge can be directly bonded to the teeth so that no tooth preparation by grinding is required. Similar bridges were constructed to replace missing upper cuspids and a lower first molar.

EXAMPLE VII

Where aesthetics are not a dominant factor, the effective fiber reinforced composite can be made utilizing continuous carbon fibers. In this example, continuous carbon filaments having a diameter of about 4 micrometers were loaded into a polymer matrix at a concentration of about 65 percent by weight. The polymeric matrix was an epoxy resin and, following the procedure of Example I, an effective fiber reinforced composite was prepared having the thickness of 0.010" and a width of about 6 inches. The resultant strips were cut to obtain a final thickness of 0.16 inch, a width of 0.030 inch and a length of several inches. The composite material was easily formed against the lingual surface of a plaster model of a dental arch by hand at room temperature. The partially polymerized material was then restrained in its position while the entire assembly was heated in a vacuum oven at 100° C. for 2 hours to cure the resin material.

As will be apparent to persons skilled in the art, various modifications, adaptations and variations of the foregoing specific disclosure can be made without departing from the teachings of the present invention.

What is claimed is:

1. In a passive dental appliance system wherein said system is selected from the group consisting of orthodontic retainers, bridges, space maintainers, tooth replacement appliances and splints, the improvement wherein a structural component thereof is fabricated as a preformed shape of high stiffness, strength, and stability, which exhibits ease of processing for subsequent application to a patient from an effective fiber-reinforced composite material comprising a polymeric matrix and a reinforcing fiber component embedded within the matrix, the reinforcing fiber component comprising at least about 30% by weight of the composite material and being substantially fully wetted by the polymer matrix, the composite material being substantially free of voids and having a modulus of elasticity greater than $0.5 \times 10^6$ psi.

2. The passive dental appliance system of claim 1 wherein the structural component is in the form of an elongated member and the fibers embedded within the matrix are at least partially aligned and oriented along the longitudinal dimension of the elongated member.

3. The passive dental appliance system of claim 1 wherein the reinforcing fiber component is selected from the group consisting of continuous filaments and short fibers of inorganic, natural and synthetic organic materials compatible with the polymeric matrix.

4. The passive dental appliance system of claim 1 wherein the reinforcing fiber component is a fiber selected from the group consisting of glass, carbon, graphite, polyaramide, polyester, and polyamide fibers.

5. The passive dental appliance system of claim 1 wherein the reinforcing fiber component has a diameter within the range of about 0.3 to 25 micrometers.

6. The passive dental appliance system of claim 1 wherein the reinforcing fiber component has a diameter within the range of about 0.3 to 20 micrometers.

7. The passive dental appliance system of claim 1 wherein the composite material has a modulus of elasticity greater than $1.0 \times 10^6$ psi.

8. The passive dental appliance system of claim 7 wherein the composite material has a modulus of elasticity up to $35 \times 10^6$ psi.

9. The passive dental appliance system of claim 1 wherein the composite material exhibits a modulus of elasticity within the range of about $1.0 \times 10^6$ psi to $60 \times 10^6$ psi.

10. The passive dental appliance system of claim 1 wherein the polymeric matrix material is selected from the group consisting of thermoplastic and thermosetting materials.

11. The passive dental appliance system of claim 1 wherein the polymeric matrix material is selected from the group consisting of polyamides, polyesters, polyester glycols, polyolefins, polyimides, polyarylates, polyurethanes, polyarylsulfides, styrene acrylonitrils, acrylonitrile-butadiene-styrene copolymers, polysulfones, polyacetals, polycarbonates, vinyl esters, and epoxies.

12. The passive dental appliance system of claim 1 wherein the reinforcing fiber component comprises up to 90% by weight of the effective composite material.

13. The passive dental appliance system of claim 1 wherein the reinforcing fiber component comprises about 30% to 80% by weight of the effective composite material.

14. The passive dental appliance system of claim 1 wherein the reinforcing fiber component comprises about 40% to 60% by weight of the composite material.

* * * * *